(12) United States Patent
Drasner et al.

(10) Patent No.: US 7,868,028 B2
(45) Date of Patent: Jan. 11, 2011

(54) GUANIDINE COMPOUNDS AS ANESTHETICS AND FOR TREATMENT OF NERVOUS SYSTEM DISORDERS

(75) Inventors: Kenneth Drasner, Kentfield, CA (US); Kevin T. Weber, Fremont, CA (US)

(73) Assignee: Fred Drasner, Miami, FL (US)

( * ) Notice: Subject to any disclaimer, the term of this patent is extended or adjusted under 35 U.S.C. 154(b) by 2691 days.

(21) Appl. No.: 10/174,055

(22) Filed: Jun. 17, 2002

(65) Prior Publication Data

US 2005/0228022 A1 Oct. 13, 2005

(51) Int. Cl.
*A01N 43/64* (2006.01)
*A61K 31/41* (2006.01)
(52) U.S. Cl. .................................................. 514/359
(58) Field of Classification Search ................ 514/360, 514/388, 395, 359
See application file for complete search history.

(56) References Cited

U.S. PATENT DOCUMENTS 5,688,830 A * 11/1997 Berger et al. ................ 514/651

FOREIGN PATENT DOCUMENTS

| EP | 1177792 | 2/2002 |
| JP | 2002155060 A2 * | 5/2002 |
| SU | 1326608 | 7/1987 |

OTHER PUBLICATIONS

Popov et al., Khimlya Geterotslklichesklkh Soedinenii (1996), (10), 1352-1357, CAPLUS Accession No. 126:47152.
Anisimova et al., Khimiko-Farmatsevticheskii Zhurnal (1987), 21(3), 313-319, CAPLUS Accession No. 1988:5879.
Anisimova et al., Khimiya-Gaterotsiklicheskikh Soedinenii (1986), (7), 918-925, CAPLUS Accession No. 1987:477696.

* cited by examiner

*Primary Examiner*—Yong S Chong
(74) *Attorney, Agent, or Firm*—Davis Wright Tremaine LLP; George C. Rondeau, Jr.

(57) ABSTRACT

Novel guanidine compounds having the formula

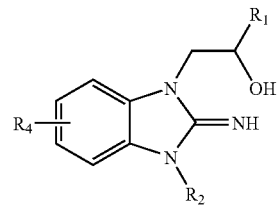

in which $R_1$, $R_2$ and $R_4$ are as defined, are effective as sodium channel blockers in neuronal mammalian cells and as anesthetics and/or analgesics, particularly local spinal and/or epidural anesthetics, for alleviation of neuropathic pain, for providing a neuroprotective effect, and for producing anticonvulsant effects.

1 Claim, No Drawings

GUANIDINE COMPOUNDS AS ANESTHETICS AND FOR TREATMENT OF NERVOUS SYSTEM DISORDERS

FIELD OF THE INVENTION

This invention relates to novel compounds that possess anesthetic and/or analgesic activity, particularly activity as local anesthetics, and more particularly activity with respect to spinal, epidural and/or other somatic or autonomic nerve conduction block. These compounds have other therapeutic applications including treatment and/or prophylaxis of neuropathic pain, epilepsy, convulsions, brain or spinal cord trauma or ischemia, and stroke.

BACKGROUND OF THE INVENTION

The leading compounds currently used as local spinal or epidural anesthetics are structurally related and include lidocaine, mepivacaine, prilocaine, chloroprocaine, bupivacaine, ropivacaine and levobupivacaine. Regional anesthesia using these compounds results from inhibition of the sodium ion influx of the voltage-gated sodium channel. These compounds have been shown to bind near the cytoplasmic opening of the sodium channel.

The natural products tetrodotoxin (TTX) and saxitoxin (STX) occlude the extracellular opening of the voltage-gated sodium channel at receptor site 1 (Lipkind, G. M., et al., *Biophys J*, 66:1-13 (1994)). Both TTX and STX are currently available only from natural sources. TTX is found in ovaries of some puffer fish species and in the eggs of the California newt. STX is produced by dinoflagellate alga species and may be found in mussels and other shellfish.

The biological activities of TTX and STX are highly selective. TTX binds to the voltage-gated sodium channel with a $K_d$ of 3 to 5 nM (Colquhoun, D., et al., *J Physiol*, 221:533-553 (1972)) while concentrations 104-fold greater have been shown to have no discernible effect on other receptors (Hille, B., *Ionic channels of excitable membranes*, (1992)). Biologic activity thus derives solely from interaction with receptor site 1 of the voltage-gated sodium channel. Compounds which compete with TTX or STX for binding to site 1 of the voltage-gated sodium channel should therefore exhibit similar biological effects.

If administered intrathecally in the rat at a dose approximating 10×$ED_{50}$ for block of the tail-flick reflex, TTX typically effects a neuronal block that lasts between two and four days. When administered intrathecally in the rat at this dose (10×$ED_{50}$ for block of tail-flick reflex), TTX appears to have toxicity to neural elements indistinguishable from saline (Sakura, S., et al., *Anesth Analg*, 81:338-346 (1995)).

In addition to anesthetic effects, compounds affecting blockade of the voltage-gated sodium channel in general, and TTX specifically, have well documented neuroprotective properties. There is substantial evidence that potentially damaging conditions such as ischemia induce influx of sodium through TTX-sensitive channels (Fung, M. L., et al., *Neurosci Lett*, 275:41-44 (1999); Lysko, P. G., et al., *Stroke*, 25:2476-2482 (1994); Taylor, C. P., et al., *Trends Pharmacol Sci*, 16:309-316 (1995)). The resultant membrane depolarization impacts other voltage-sensitive mechanisms such as voltage-sensitive calcium channels, potassium channels, and glutamate release (Li, S., et al., *J Neurosci*, 19:RC16 (1999)). Membrane depolarization further enhances sodium entry leading to high concentrations of intracellular sodium, depletion of ATP stores, and influx of calcium via reversal of the $Na^+$—$Ca^{2+}$ exchanger. The deleterious condition need not be acute because TTX has been shown to protect motor neurons in a chronic model of glutamate toxicity developed to mimic ALS (Rothstein, J. D., et al., *Proc Natl Acad Sci USA*, 90:6591-6595 (1993)).

Regardless of underlying mechanism, the homeostatic, cytoprotective, and beneficial physiologic effects afforded by TTX has been demonstrated in a variety of in vitro and in vivo biological models using varied insults including vascular occlusion (Yamasaki, Y., et al., *Neurosci Lett*, 121:251-254 (1991)), cardiac arrest (Prenen, G. H., et al., *Exp Neurol*, 99:118-132 (1988)), traumatic axonal deformation (Wolf, J. A., et al., *J Neurosci*, 21:1923-1930 (2001)), dorsal column segment compression (Agrawal, S. K., et al., *J Neurosci*, 16:545-552 (1996)), anoxia (Breder, J., et al., *Neuropharmacology*, 39:1779-1787 (2000); Imaizumi, T., et al., *J Neurotrauma*, 14:299-311 (1997); Lopachin, R. M., *Ann NY Acad Sci*, 890:191-203 (1999); LoPachin, R. M., et al., *Neuroscience*, 103:971-983 (2001); Pringle, A. K., et al., *Brain Res*, 755:36-46 (1997); Probert, A. W., et al., *Neuropharmacology*, 36:1031-1038 (1997); Stys, P. K., et al., *Ann Neurol*, 30:375-380 (1991); Stys, P. K., et al., *J Neurosci*, 12:430-439 (1992); Vornov, J. J., et al., *Stroke*, 25:457-464 (1994); Waxman, S. G., et al., *Brain Res*, 644:197-204 (1994); Weber, M. L., et al., *Brain Res*, 664:167-177 (1994)), glucose deprivation (Tasker, R. C., et al., *J Neurosci*, 12:4298-4308 (1992)) as well as excitotoxic damage induced by veratridine (Lysko, P. G., et al., *Stroke*, 25:2476-2482 (1994)), brevetoxins (Berman, F. W., et al., *J Pharmacol Exp Ther*, 290:439-444 (1999)), and NMDA receptor stimulation (Skaper, S. D., et al., *J Neurochem*, 76:47-55 (2001); Strijbos, P. J., et al., *J Neurosci*, 16:5004-5013 (1996)).

Compounds effective at blocking voltage-gated sodium channels are effective in the treatment of neuropathic pain. More specifically, TTX inhibits neuropathic ectopic activity by blockage of TTX-sensitive voltage-gated sodium channels accumulating at the site of injury (Kim, C. H., et al., *Brain Res Mol Brain Res*, 95:153-161 (2001); Omana-Zapata, I., et al., *Pain*, 72:41-49 (1997)). In-vivo administration of TTX significantly reduces allodynic behavior in a rat model (Lyu, Y. S., et al., *Brain Res*, 871:98-103 (2000)). Consistent with this, TTX has been used effectively to reduce neuropathic pain in patients with cancer (du Souich, P., et al., *Clin. Pharmacol. Ther.*, 71:MPI-46 (2002)).

Voltage-gated sodium channel blockers have also been shown effective against partial and generalized tonic seizures (Catterall, W. A., *Adv Neurol*, 79:441-456 (1999)). More specifically, TTX has been shown to suppress seizures in rat hippocampal slices for several hours (Burack, M. A., et al., *Epilepsy Res*, 22:115-126 (1995)).

A compound that competes for binding to the voltage-gated sodium channel with TTX can be an anesthetic, an analgesic, a neuroprotective agent, an agent for treatment of neuropathic pain, or an anticonvulsant. Such is the case with the compounds described here.

BRIEF SUMMARY OF THE INVENTION

The invention provides a new method and new compositions for producing anesthesia or analgesia in a subject. The method comprises administering to said subject an anesthetically or analgesically effective amount of one or more compounds having the formula

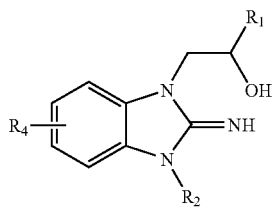

in which:

R₁ is
(a) substituted or unsubstituted alkyl;
(b) substituted or unsubstituted cycloalkyl;
(c) substituted or unsubstituted alkenyl;
(d) adamantyl;
(e) substituted or unsubstituted phenyl;
(f) a 5- or 6-membered optionally substituted saturated or unsaturated heterocyclic group having from one to three heteroatoms selected from nitrogen, oxygen and sulfur;
(g) substituted or unsubstituted benzyl;
(h) a saturated or unsaturated fused ring carbocyclic group having from 8 to 10 ring atoms; or
(i) $CH_2XR_5$, where X is oxygen, sulfur, —NH— or —$CH_2$— and $R_5$ is substituted or unsubstituted alkyl; substituted or unsubstituted cycloalkyl; substituted or unsubstituted phenyl; substituted or unsubstituted benzyl; 2-carbamide-indolyl; or a 5- to 9-membered optionally substituted saturated or unsaturated heterocyclic group having from one to three heteroatoms selected from nitrogen, oxygen and sulfur;

R₂ is
(a) substituted or unsubstituted alkyl;
(b) substituted or unsubstituted cycloalkyl;
(c) substituted or unsubstituted alkenyl;
(d) substituted or unsubstituted alkoxyalkyl
(e) a 5- or 6-membered optionally substituted saturated or unsaturated heterocyclic group having from one to three heteroatoms selected from nitrogen, oxygen and sulfur;
(f) —$(CH_2)_nR_3$, where $R_3$ is (i) a 5- to 9-membered optionally substituted saturated or unsaturated heterocyclic group having from one to three heteroatoms selected from nitrogen, oxygen and sulfur; (ii) —$NR_6R_7$ where $R_6$ and $R_7$ are independently selected from hydrogen, methyl, ethyl and benzyl; or (iii) $COOR_8$ where $R_8$ is alkyl; and n is 2 or 3;
(g) substituted or unsubstituted phenyl;
(h) substituted or unsubstituted benzyl;
(j) a saturated or unsaturated fused ring carbocyclic group having from 8 to 10 ring atoms; or
(k) methylene-1-naphthyl;

and R₄ is
(a) hydrogen;
(b) $(CH_2)_mCOOR_{15}$ where $R_{15}$ is alkyl or substituted alkyl; and m is 0, 1 or 2;
(c) $CONR_{16}R_{17}$ where $R_{16}$ and $R_{17}$ are independently (i) hydrogen; (ii) alkyl or substituted alkyl; (iii) cycloalkyl; (iv) alkoxyalkyl; (v) a 5- to 10-membered optionally substituted saturated or unsaturated heterocyclic group having from one to three heteroatoms selected from nitrogen, oxygen and sulfur; (vi) a saturated or unsaturated fused ring carbocyclic group having from 8 to 10 ring atoms; (vii) substituted or unsubstituted phenyl; (viii) $(CH_2)_pR_{18}$ where $R_{18}$ is a 5- or 6-membered optionally substituted saturated or unsaturated heterocyclic group having from one to three heteroatoms selected from nitrogen, oxygen and sulfur, and p is 1, 2 or 3; (ix) optionally substituted benzyl; or (x) an aralkyl group comprising a chain of from 1 to 4 methylene groups substituted by one or two phenyl groups;
(d) $C_1$-$C_4$ alkoxy;
(e) optionally substituted phenoxy;
(f) $SO_2NR_{19}R_{20}$ where $R_{19}$ and $R_{20}$ are independently hydrogen, optionally substituted alkyl or phenyl;
(g) $NR_{21}R_{22}$;
(h) $COR_{23}$ where $R_{23}$ is alkyl or is $NR_{21}R_{22}$;
(j) $COOR_{23}$ where $R_{23}$ is hydrogen, alkyl, or benzyl; or
(k) $SO_2R_{25}$ where $R_{25}$ is alkyl or $NR_{21}R_{22}$;
wherein $R_{21}$ and $R_{22}$ are independently hydrogen, alkyl, optionally substituted phenyl or optionally substituted benzyl;
or a pharmaceutically acceptable salt thereof.

This invention further provides pharmaceutical compositions, particularly anesthetic or analgesic compositions, containing one or more compounds as defined above, together with one or more pharmaceutically acceptable diluents or carriers, and optionally also including other pharmaceutically suitable ingredients. In a preferred embodiment the compositions contain an effective amount of such a compound; however, the invention also includes more concentrated compositions containing these compounds that may be diluted to provide single-dosage units containing an anesthetically or analgesically effective amount. The invention further provides an effective composition according to this invention contained within a pharmaceutically acceptable container, for example one used in preparing single-dosage units of compounds for use as anesthetics or analgesics.

The invention further provides a method for blocking voltage-gated sodium channels of neuronal mammalian cells in general, and compositions for carrying out such a method, wherein the method and compositions involve use of the above-described compounds.

Compounds that modulate the function of the sodium channel have a number of therapeutic applications, including the use in anesthesia, analgesia and the treatment and/or prophylaxis of neuropathic pain, epilepsy, convulsions, brain or spinal cord ischemia, brain or spinal cord trauma, and stroke.

The invention further provides methods for providing a neuroprotective effect to a subject, and compositions for carrying out such a method, wherein the method and compositions involve use of the above-described compounds.

The invention further provides methods for treating or alleviating neuropathic pain in a subject, and compositions for carrying out such a method, wherein the method and compositions involve use of the above-described compounds.

Still further, the invention provides methods for providing an anticonvulsant treatment or effect to a subject, or for treating seizures in a subject, and compositions for carrying out such a method, wherein the method and compositions involve use of the above-described compounds.

The invention further provides processes and chemical intermediates for producing the above compounds.

DEFINITIONS

As used herein, terms have the following meanings:
Anesthetic: providing loss of sensation or numbness.
Local anesthetic: Local anesthetics produce loss of sensation or numbness in a localized area of the body. The term includes, but is not limited to, a compound or composition that, when locally administered, e.g., topically by infiltration, or when injected to make contact with a nerve, provides full or partial inhibition of sensory perception and/or motor function. Under either definition, the localized condition so induced is also referred to herein as "local anesthesia". Local anesthesia can result, for example, from contact of an effective amount of a local anesthetic with sensory nerve processes at the site at which the painful stimulus is present, or can result from inhibition of nerve transmission at a nerve or nerves proximal to the site at which the painful stimulus is present The mechanism by which local anesthetics induce their effect is generally thought to be based primarily upon the ability to interfere with the initiation or transmission of the nerve impulse. The duration of action of a local anesthetic is generally proportional to the time during which it is in actual contact with the nervous tissues.

Anesthetically effective amount: An amount of a compound or composition that produces an anesthetic effect, that is, a partial or total loss of sensation, inhibition of sensory perception or inhibition of motor function.

Analgesia: Reduction of pain, generally.

Analgesically effective amount: An amount of a compound or composition that produces a reduction of pain or a full elimination of pain, in a patient.

Neuroprotective: The effect of reducing, arresting or ameliorating nervous insult, and protecting, resuscitating, or reviving nervous tissue that has suffered nervous insult.

Nervous insult or "insult" refers to any damage or potentially damaging influence to nervous tissue and any disability or death resulting therefrom. The cause of nervous insult may include but is not limited to metabolic, toxic, thermal, biochemical, chemical, and apoptotic and includes without limitation, ischemia, hypoxia, glutamate abnormality and secondary effects thereof, cerebrovascular accident, trauma, surgery, pressure, mass effect, hemorrhage, radiation, vasospasm, epilepsy, myelination/demyelination process, infection, cognitive disorder, and neurodegenerative disease such as Parkinson's disease and amyotrophic lateral sclerosis (ALS).

Neuropathic pain: Pain caused by aberrant somatosensory processing in the peripheral or central nervous system. Chronic or debilitating conditions, such as post-herpetic neuralgia and phantom limb syndrome, are categorized as neuropathic pain.

Anticonvulsant: Prevention, treatment, or attenuation of seizures or convulsions due to abnormal electrical activity in the nerve cells of the brain. These seizures may be provoked such as might occur with fever or metabolic disturbance, or unprovoked as occurs in epilepsy. They may be generalized involving all of the brain, or be partial or focal, being limited to one part of the brain. They may be manifest by sudden, violent, uncontrollable contraction of muscles as may occur with generalized tonic-clonic seizures, or more subtle, such as occurs with petit mal, partial complex, or temporal lobe seizures.

Patient or subject: A human (or other animal) that is to be treated using the compounds, compositions and/or methods disclosed herein.

Alkyl, alkoxy, alkoxyalkyl, alkylthio: saturated acyclic moieties, with straight or branched chains, having the indicated number of carbon atoms. Alkyl groups are hydrocarbyl moieties; alkoxy and alkoxyalkyl groups have an oxygen atom in the chain; alkylthio groups have a sulfur atom in the chain. Examples include methyl, ethyl, and the various propyl, butyl, pentyl, hexyl and octyl groups, methoxy, ethoxy, n-propoxy, isopropoxy, methoxymethyl, ethoxymethyl, n-propoxyethyl, methylthio, ethylthio, n-propylthio and n-butylthio.

Alkyleneoxy; alkylenedioxy: includes methylenedioxy, —OCH$_2$O—, ethylenedioxy, —OCH$_2$CH$_2$O— and ethyleneoxy, —CH$_2$CH$_2$O—.

Cycloalkyl: saturated cyclic hydrocarbyl moieties, analogous to alkyl groups, having the indicated number of carbon atoms. Examples include cyclopropyl, cyclobutyl, cyclopentyl, cyclohexyl, cycloheptyl and cylooctyl.

Alkenyl: Unsaturated acyclic hydrocarbyl moieties, with straight or branched chains, containing one or more double (olefinic) bonds, and having the indicated number of carbon atoms. Examples include vinyl, allyl, isopropenyl, 2-butenyl, 1,3-butadienyl, and the various pentenyl, hexenyl and octenyl groups.

Alkyl, alkenyl cycloalkyl and other aliphatic groups may be unsubstituted or may be substituted. Typical substituents include halo, hydroxy, cyano, nitro, COOH and COOCH$_3$. Substituted moieties may have from one to as many substituents as are possible on the group in question. Preferably, substituted alkyl, alkenyl and cycloalkyl moieties have from 1 to 4 substituents (of course, with a maximum number of substituents possible for the group in question). In polysubstituted compounds the substituents may be the same or different, i.e. an alkyl group may be substituted with two or three different halogens, or with halo and hydroxy groups.

Aralkyl: as generally used, refers to an alkyl group having an aryl substituent. Aralkyl groups in compounds of the present invention and their compositions and uses have the general formula $(CH_2)_{1-4}Ph_{1-2}$ where Ph stands for phenyl. That is, they have from 1 to 4 methylene groups in a chain, substituted by one or two phenyl groups. An example of such an aralkyl group is 3,3-diphenylpropyl.

Halo includes fluoro, chloro, bromo and iodo substituents as indicated. Where a moiety or compound includes multiple halogens, they may be the same or different; i.e. such a compound or moiety may contain two or more different halogen atoms.

Fused carbocyclic ring moieties include fully or partly unsaturated rings such as naphthyl, tetrahydronapthyl and phenyl substituted by alkylene groups having 2-4 carbon atoms. One example of the last-mentioned type of fused ring is indanyl, i.e. a phenyl ring substituted with a propylene (—CH$_2$CH$_2$CH$_2$—) moiety.

Heterocyclic moieties include both saturated and unsaturated cyclical moieties having the indicated number of members, or atoms, including one or more nitrogen, sulfur and/or oxygen atoms, as indicated. The remaining atoms in the ring are carbon atoms. The moieties may contain the atoms in a single ring or in a fused ring. Examples of five-membered heterocyclic rings include thienyl, furyl, tetrahydrofuryl, oxazolyl, isoxazolyl, thiazolyl, isothiazolyl, thiazolidinyl, pyrrolyl, pyrrolidinyl, pyrrolinyl, imidazolyl, imidazolidinyl, pyrazolyl, triazolyl, and pyrazolidinyl. Examples of six-membered heterocyclic rings include pyridyl, pyrazinyl, pyrimidinyl, triazinyl, piperidyl, morpholinyl, pyranyl, tetrahydropyranyl, and piperazinyl.

Examples of heterocyclic moieties having more than six carbons include indolyl, quinuclidyl, quinolyl, chromanyl, benzimidazolyl, benzoxazolyl, benzothienyl, benzofuranyl, and quinolinyl.

Heterocyclic moieties may be unsubstituted or may be substituted, for instance, by from 1 to 3 groups independently selected from halo, $C_1$-$C_4$ alkyl, hydroxy, or oxo, including combinations of such substituents.

Unsaturated moieties include in the case of carbocyclic and heterocyclic rings partially unsaturated moieties such as 1,2, 3,4-tetrahydropyridinyl and 2,3-dihydroindolyl, and fully unsaturated moieties such as pyridinyl and indolyl.

DETAILED DESCRIPTION OF THE INVENTION

This invention also provides anesthetic and/or analgesic compositions and methods, as well as certain novel anesthetic and/or analgesic compounds.

In one aspect, the invention provides a method for producing anesthesia or analgesia in a subject. The method comprises administering to said subject an anesthetically or analgesically effective amount of a compound having the formula

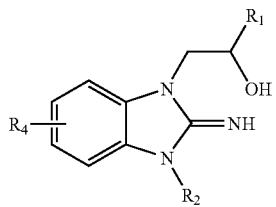

in which:

$R_1$ is
(a) substituted or unsubstituted alkyl;
(b) substituted or unsubstituted cycloalkyl;
(c) substituted or unsubstituted alkenyl;
(d) adamantyl;
(e) substituted or unsubstituted phenyl;
(f) a 5- or 6-membered optionally substituted saturated or unsaturated heterocyclic group having from one to three heteroatoms selected from nitrogen, oxygen and sulfur;
(g) substituted or unsubstituted benzyl;
(h) a saturated or unsaturated fused ring carbocyclic group having from 8 to 10 ring atoms; or
(j) $CH_2XR_5$, where X is oxygen, sulfur, —NH— or —$CH_2$— and $R_5$ is substituted or unsubstituted alkyl; substituted or unsubstituted cycloalkyl; substituted or unsubstituted phenyl; substituted or unsubstituted benzyl; 2-carbamide-indolyl; or a 5- to 9-membered optionally substituted saturated or unsaturated heterocyclic group having from one to three heteroatoms selected from nitrogen, oxygen and sulfur;

$R_2$ is
(a) substituted or unsubstituted alkyl;
(b) substituted or unsubstituted cycloalkyl;
(c) substituted or unsubstituted alkenyl;
(d) substituted or unsubstituted alkoxyalkyl
(e) a 5- or 6-membered optionally substituted saturated or unsaturated heterocyclic group having from one to three heteroatoms selected from nitrogen, oxygen and sulfur;
(f) —$(CH_2)_nR_3$, where $R_3$ is (i) a 5- to 9-membered optionally substituted saturated or unsaturated heterocyclic group having from one to three heteroatoms selected from nitrogen, oxygen and sulfur; (ii) —$NR_6R_7$ where $R_6$ and $R_7$ are independently selected from hydrogen, methyl, ethyl and benzyl; or (iii) $COOR_8$ where $R_8$ is alkyl; and n is 2 or 3;
(g) substituted or unsubstituted phenyl;
(h) substituted or unsubstituted benzyl;
(j) a saturated or unsaturated fused ring carbocyclic group having from 8 to 10 ring atoms; or
(k) methylene-1-naphthyl;
and $R_4$ is
(a) hydrogen;
(b) $(CH_2)_mCOOR_{15}$ where $R_{15}$ is alkyl or substituted alkyl; and m is 0, 1 or 2;

(c) $CONR_{16}R_{17}$ where $R_{16}$ and $R_{17}$ are independently (i) hydrogen; (ii) alkyl or substituted alkyl; (iii) cycloalkyl; (iv) alkoxyalkyl; (v) a 5- to 10-membered optionally substituted saturated or unsaturated heterocyclic group having from one to three heteroatoms selected from nitrogen, oxygen and sulfur; (vi) a saturated or unsaturated fused ring carbocyclic group having from 8 to 10 ring atoms; (vii) substituted or unsubstituted phenyl; (viii) $(CH_2)_pR_{18}$ where $R_{18}$ is a 5- or 6-membered optionally substituted saturated or unsaturated heterocyclic group having from one to three heteroatoms selected from nitrogen, oxygen and sulfur, and p is 1, 2 or 3; (ix) optionally substituted benzyl; or (x) an aralkyl group comprising a chain of from 1 to 4 methylene groups substituted by one or two phenyl groups;
(d) $C_1$-$C_4$ alkoxy;
(e) optionally substituted phenoxy;
(f) $SO_2NR_{19}R_{20}$ where $R_{19}$ and $R_{20}$ are independently hydrogen, optionally substituted alkyl or phenyl;
(g) $NR_{21}R_{22}$;
(h) $COR_{23}$ where $R_{23}$ is alkyl or is $NR_{21}R_{22}$;
(j) $COOR_{23}$ where $R_{23}$ is hydrogen, alkyl, or benzyl; or
(k) $SO_2R_{25}$ where $R_{25}$ is alkyl or $NR_{21}R_{22}$;
wherein $R_{21}$ and $R_{22}$ are independently hydrogen, alkyl, optionally substituted phenyl or optionally substituted benzyl;
or a pharmaceutically acceptable salt thereof.

In a second aspect, the invention provides pharmaceutical compositions, particularly anesthetic or analgesic compositions, containing one or more compounds as defined herein, together with one or more pharmaceutically acceptable diluents or carriers, and optionally also including other pharmaceutically suitable ingredients. In a preferred embodiment the compositions contain an effective amount of such a compound; however, the invention also includes more concentrated compositions containing these compounds that may be diluted to provide single-dosage units containing an anesthetically or analgesically effective amount. The invention further provides an effective composition according to this invention contained within a pharmaceutically acceptable container, for example one used in preparing single-dosage units of compounds for use as anesthetics or analgesics. More preferably, the invention involves compositions, particularly anesthetic and/or analgesic compositions, and anesthetic and/or analgesic methods that involve the inclusion, or the administration to a patient, respectively, of one or more compounds having the formula

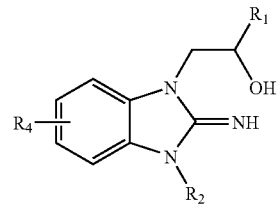

in which:

$R_1$ is
(a) $C_1$-$C_6$ alkyl, optionally substituted with one or more groups selected from halo, hydroxy, cyano, nitro, COOH and $COOCH_3$;
(b) $C_2$-$C_6$ alkenyl, optionally substituted with one or more groups selected from halo, hydroxy, cyano, nitro, COOH and $COOCH_3$;
(c) $C_3$-$C_6$ cycloalkyl, optionally substituted with one or more groups selected from halo, hydroxy, cyano, nitro, COOH and $COOCH_3$;

9

(d) adamantyl;
(e) optionally substituted phenyl in which the substituents are selected from mono- and dihalo, mono- and di-($C_1$-$C_4$ alkoxy), mono- and di-($C_1$-$C_4$ alkylthio), $C_1$-$C_2$ alkyleneoxy; $C_1$-$C_2$ alkylenedioxy, mono- and di-($C_1$-$C_4$ alkyl), mono- and di-(trifluoromethyl), mono- and di-($C_1$-$C_4$ hydroxyalkyl), mono- and di-($C_1$-$C_4$ alkoxyalkyl), mono- and di-hydroxy, mono- and di-cyano, mono- and di-($COCH_3$), and mono- and di-$NHR_{26}$;
(f) a 5- or 6-membered saturated or unsaturated heterocyclic group having from one to three heteroatoms selected from nitrogen, oxygen and sulfur, optionally substituted by from 1 to 3 groups independently selected from halo, $C_1$-$C_4$ alkyl, $C_1$-$C_4$ alkoxy, oxo and hydroxy;
(g) optionally substituted benzyl in which the substituents are selected from mono- and dihalo, mono- and di-($C_1$-$C_4$ alkoxy), mono- and di-($C_1$-$C_4$ alkylthio), $C_1$-$C_2$ alkyleneoxy; $C_1$-$C_2$ alkylenedioxy, mono- and di-($C_1$-$C_4$ alkyl), mono- and di-(trifluoromethyl), mono- and di-($C_1$-$C_4$ hydroxyalkyl), mono- and di-($C_1$-$C_4$ alkoxyalkyl), mono- and di-hydroxy, mono- and di-cyano, mono- and di-($COCH_3$), and mono- and di-$NHR_{26}$;
(g) naphthyl; or
(h) $CH_2XR_5$, where X is oxygen, sulfur, —NH— or —$CH_2$— and $R_5$ is selected from (i) $C_1$-$C_6$ alkyl; (ii) $C_3$-$C_6$ cycloalkyl; (iii) optionally substituted phenyl in which the substituents are selected from mono- and di-($C_1$-$C_4$ alkyl), mono- and dihalo, mono- and di-($C_1$-$C_4$ alkoxy), $C_1$-$C_2$ alkyleneoxy, $C_1$-$C_2$ alkylenedioxy, mono- and di-(trifluoromethyl), nitro, hydroxy, mono- and di-($C_1$-$C_4$ hydroxyalkyl), mono- and di-($C_1$-$C_4$ alkoxyalkyl), mono- and di-hydroxy, mono- and dicyano, mono- and di-($COCH_3$) and mono- and di-$NHR_{26}$; (iv) benzyl; (v) 2-carbamide-indolyl; or (vi) a 5- to 9-membered saturated or unsaturated heterocyclic group having from one to three heteroatoms selected from nitrogen, oxygen and sulfur, optionally substituted by from 1 to 3 groups independently selected from halo, $C_1$-$C_4$ alkyl, $C_1$-$C_4$ alkoxy, oxo and hydroxy;

$R_2$ is (a) $C_1$-$C_{12}$ alkyl, optionally substituted with one or more groups selected from halo, hydroxy, cyano, nitro, COOH and $COOCH_3$;
(b) $C_2$-$C_8$ cycloalkyl, optionally substituted with one or more groups selected from halo, hydroxy, cyano, nitro, COOH and $COOCH_3$;
(c) $C_2$-$C_{12}$ alkenyl, optionally substituted with one or more groups selected from halo, hydroxy, cyano, nitro, COOH and $COOCH_3$;
(d) $C_2$-$C_{12}$ alkoxyalkyl;
(e) a 5- or 6-membered saturated or unsaturated heterocyclic group having from one to three heteroatoms selected from nitrogen, oxygen and sulfur, optionally substituted by from 1 to 3 groups independently selected from halo, $C_1$-$C_4$ alkyl, $C_1$-$C_4$ alkoxy, oxo, and hydroxy;
(f) —$(CH_2)_nR_3$, where $R_3$ is (i) a 5- to 9-membered saturated or unsaturated heterocyclic group having from one to three heteroatoms selected from nitrogen, oxygen and sulfur, optionally substituted by from 1 to 3 groups independently selected from halo, $C_1$-$C_4$ alkyl, $C_1$-$C_4$ alkoxy, oxo, and hydroxy; (ii) —$NR_6R_7$ where $R_6$ and $R_7$ are independently selected from hydrogen, methyl, ethyl and benzyl; or (iii) $COOR_8$ where $R_8$ is $C_1$-$C_4$ alkyl; and n is 2 or 3;
(g) optionally substituted phenyl, where the substituents are independently selected from mono- and di-($C_1$-$C_4$ alkyl); mono- and dihalo; mono-, di-, and tri-($C_1$-$C_4$ alkoxy); mono- and dicyano; nitro; methylsulfonyl; mono-, di-, and tri-(trifluoromethyl); $C_1$-$C_2$ alkyleneoxy; $C_1$-$C_2$ alkylenedioxy; —$(CH_2)_qCOOR_9$ where $R_9$ is $C_1$-$C_4$ alkyl; or —$(CH_2)_qNR_{10}R_{11}$ where $R_{10}$ and $R_{11}$ are independently selected from hydrogen, ($C_1$-$C_4$) alkyl, $COR_{12}$ where $R_{12}$ is $C_1$-$C_4$ alkyl, $SO_2R_{13}$ where $R_{13}$ is $C_1$-$C_4$ alkyl, or $COOR_{14}$ where $R_{14}$ is $C_1$-$C_4$ alkyl and CONR'R''; and q is an integer from 1 to 4;
(h) optionally substituted benzyl, where the substituents are selected from mono-, di-, and tri-($C_1$-$C_4$) alkyl; mono-, di-, and tri-halo; mono-, di-, and tri-($C_1$-$C_4$ alkoxy); mono-, di-, and tri-($C_1$-$C_4$ alkylthio); mono- and di-cyano; nitro; methylsulfonyl; mono-, di-, and tri-(trifluoromethyl); mono-, di-, and tri-COOR'; mono-, di-, and tri-CONR'R''; mono-, di-, and tri-$NR_{27}R_{28}$ where $R_{27}$ and $R_{28}$ are independently selected from hydrogen, $C_1$-$C_4$ alkyl, acetyl, and methylsulfonyl; $C_1$-$C_2$ alkyleneoxy; $C_1$-$C_2$ alkylenedioxy; and mono-, di-, and tri-($C_1$-$C_6$ alkoxyalkyl);
(j) a saturated or unsaturated fused ring carbocyclic group having from 8 to 10 ring atoms; or
(k) methylene-1- or 2-naphthyl; and $R_4$ is (a) hydrogen;
(b) $(CH_2)_mCOOR'$ where m is 0, 1 or 2;
(c) $CONR_{16}R_{17}$ where $R_{16}$ and $R_{17}$ are independently (i) hydrogen; (ii) $C_1$-$C_5$ alkyl optionally substituted with one or more groups selected from halo, hydroxy, cyano, nitro, COOH and $COOCH_3$; (iii) $C_3$-$C_6$ cycloalkyl; (iv) $C_2$-$C_8$ alkoxyalkyl; (v) a 5- to 10-membered saturated or unsaturated heterocyclic group having from one to three heteroatoms selected from nitrogen, oxygen and sulfur, optionally substituted by from 1 to 3 groups independently selected from halo, hydroxy, oxo, $C_1$-$C_4$ alkyl, $C_1$-$C_4$ alkoxy, $COCH_3$, COOR', and $NR_{29}R_{30}$ where $R_{29}$ and $R_{30}$ are independently selected from hydrogen, $C_1$-$C_4$ alkyl, acetyl, or methylsulfonyl; (vi) a saturated or unsaturated fused ring carbocyclic group having from 8 to 10 ring atoms; (vii) $(CH_2)_pR_{18}$ where $R_{18}$ is a 5- or 6-membered saturated or unsaturated heterocyclic group having from 1 to 3 heteroatoms selected from nitrogen, oxygen and sulfur, optionally substituted by from 1 to 3 groups independently selected from halo, hydroxy, $C_1$-$C_4$ alkyl, $C_1$-$C_4$ alkoxy and oxo, and p is 1, 2 or 3; (viii) phenyl optionally substituted by one or more groups independently selected from mono-, di-, and tri-halo, mono-, di-, and tri-hydroxy, mono-, di-, and tri-($C_1$-$C_4$ alkyl), $C_1$-$C_2$ alkyleneoxy, $C_1$-$C_2$ alkylenedioxy, COOR', and $NR_{29}R_{30}$ where $R_{29}$ and $R_{30}$ are independently selected from hydrogen, $C_1$-$C_4$ alkyl, acetyl, and methylsulfonyl; (ix) optionally substituted benzyl where the substituents are selected from mono-, di-, and tri-($C_1$-$C_4$ alkyl); mono-, di-, and tri-halo; mono-, di-, and tri-($C_1$-$C_4$ alkoxy); nitro; methylsulfonyl; mono-, di-, and tri-(trifluoromethyl); NR'R''; $C_1$-$C_2$ alkyleneoxy; $C_1$-$C_2$ alkylenedioxy; (x) an aralkyl group comprising a chain of from 1 to 4 methylene groups substituted by one or two phenyl groups;
(d) $C_1$-$C_4$ alkoxy;
(e) optionally substituted phenoxy, where the substituents are independently selected from mono- and di-($C_1$-$C_4$) alkyl; mono- and dihalo; mono-, di-, and tri-($C_1$-$C_4$ alkoxy); cyano; nitro; methylsulfonyl; mono-, di-, and tri-trifluoromethyl; $C_1$-$C_2$ alkyleneoxy; $C_1$-$C_2$ alkylenedioxy; —$(CH_2)_rCOOR_9$ where $R_9$ is $C_1$-$C_4$ alkyl; or —$(CH_2)_rNR_{30}R_{31}$ where $R_{30}$ and $R_3$, are independently hydrogen, ($C_1$-$C_4$) alkyl, $COR_{32}$ where $R_{32}$ is $C_1$-$C_4$ alkyl, $SO_2R_{33}$ where $R_{33}$ is $C_1$-$C_4$ alkyl, or $COOR_{34}$ where $R_{34}$ is $C_1$-$C_4$ alkyl;

(f) $SO_2NR_{35}R_{36}$ where $R_{35}$ and $R_{36}$ are independently hydrogen, $C_1$-$C_4$ alkyl or phenyl; or (g) $NR_{37}R_{38}$ where $R_{37}$ and $R_{38}$ are independently hydrogen; $C_1$-$C_4$ alkyl; phenyl; $COR_{39}$ where $R_{39}$ is $C_1$-$C_4$ alkyl; or $SO_2R_{40}$ where $R_{40}$ is hydrogen or $C_1$-$C_4$ alkyl;

wherein $R_{26}$ is $COCH_3$, $SO_2CH_3$, $SO_2C_6H_5$, COOR' or CONR'R''; and wherein R' and R'' are independently hydrogen or $C_1$-$C_4$ alkyl;

and pharmaceutically acceptable salts thereof.

Particularly preferred compounds, compositions and methods are those:

in which $R_1$ is phenyl, substituted phenyl (compounds in which $R_1$ is unsubstituted phenyl and mono- or dihalophenyl being especially preferred), heterocyclic groups (thienyl being especially preferred), or $CH_2XR_5$, (especially preferred are those compounds where X is oxygen and $R_5$ is substituted or unsubstituted phenyl or is benzyl);

in which $R_2$ is benzyl, substituted benzyl, $C_2$-$C_4$ alkyl, or —$(CH_2)_2R_3$, where $R_3$ is a 5- to 6-membered saturated or unsaturated heterocyclic group having from one to three heteroatoms selected from nitrogen, oxygen and sulfur (2-N-piperidoethyl being most preferred of these);

and in which $R_4$ is hydrogen;

or in which $R_1$, $R_2$ and $R_4$ are combinations of these preferred subgroups.

Table 1 below includes representative compounds of this series. A number of the compounds in this table are available from commercial or non-profit organizations that market such molecules without regard to any specific use. They are purchased for various purposes, including use as chemical intermediates or for screening for supposed activity. These compounds thus are not novel per se; however to date no pharmaceutical activity has been reported for them.

Other compounds, as indicated in Table 1, are novel. These compounds were prepared, for example, by the process described below. Their structures were confirmed by spectroscopic analysis.

The novel compounds are those
in which $R_1$ is phenoxymethyl and $R_2$ is 4-fluorobenzyl, 4-methoxybenzyl, 2-N-piperidoethyl, octyl, 1-naphthylmethyl, n-undecyl, benzyl or 2-(N,N-dibenzylamino)ethyl;

in which $R_1$ is benzyloxymethyl, in which $R_1$ and $R_2$ are both benzyl and all those in which $R_4$ is other than hydrogen.

As shown, the compounds in Table 1 were purchased or made, and tested, in the form of salts, particularly the hydrochloride and hydrobromide salts. However, this was done for convenience, and the invention is not limited to the use of these or other salts, but encompasses the compounds per se as well as their pharmaceutically acceptable salts.

TABLE 1

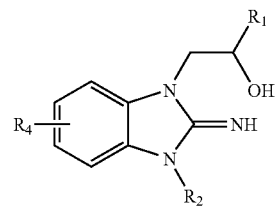

| Compound no./salt | $R_1$ | $R_2$ | R4 |
|---|---|---|---|
| 1/hydrochloride | —$CH_2O(4$-$ClC_6H_4)$ (4-chlorophenoxymethyl) | benzyl | H |
| 2/hydrochloride | 3,4-dichlorophenyl | benzyl | H |
| 3/hydrochloride | —$CH_2OC_6H_5$ (phenoxymethyl) | benzyl | H |
| 4/hydrochloride | phenoxymethyl | 4-methylbenzyl | H |
| 5/hydrochloride | phenyl | benzyl | H |
| 6/hydrochloride | 2-thiophenyl | benzyl | H |
| 7/hydrochloride | 4-chlorophenyl | benzyl | H |
| 8/hydrochloride | phenoxymethyl | n-butyl | H |
| 9/hydrochloride | 3,4-dichlorophenyl | ethyl | H |
| 10/hydrochloride | 4-chlorophenoxymethyl | n-butyl | H |
| 11/hydrochloride | 3,4-dichlorophenyl | 4-methylbenzyl | H |
| 12/hydrochloride | phenoxymethyl | 4-t-butylbenzyl | H |
| 13/hydrochloride | 3,4-dichlorophenyl | methyl | H |
| 14/hydrochloride | phenoxymethyl | 4-chlorobenzyl | H |
| 15/hydrochloride | 4-chlorophenoxymethyl | 4-chlorobenzyl | H |
| 16/hydrochloride | 2-thienyl | 2-(1-morpholino)ethyl | H |
| 17/hydrochloride | 2-thienyl | ethyl | H |
| 18/hydrochloride | phenyl | n-butyl | H |
| 19/hydrochloride | phenoxymethyl | ethyl | H |
| 20/hydrochloride | phenoxymethyl | n-propyl | H |
| 21/hydrochloride | p-chlorophenoxymethyl | ethyl | H |
| 22/hydrochloride | phenoxymethyl | 2-(1-piperido)ethyl | H |
| 23/hydrochloride | (1-?) adamantyl | methyl | H |
| 24/hydrochloride | methyl | benzyl | H |
| 25/hydrochloride | 2-furyl | 2-(1-morpholino)ethyl | H |
| 26/hydrochloride | t-butyl | benzyl | H |
| 27/hydrochloride | 4-methoxyphenyl | methyl | H |
| 28/hydrochloride | 4-methylphenyl | 2-(N,N-diethylamino)ethyl | H |
| 29/hydrochloride | 4-chlorophenoxymethyl | n-propyl | H |
| 30/hydrochloride | phenyl | 2-(1-piperido)ethyl | H |
| 31/hydrochloride | 3,4-dimethoxyphenyl | 2-(N,N-diethylamino)ethyl | H |
| 32/hydrochloride | 1-naphthyl | 2-(1-piperido)ethyl | H |
| 33/hydrochloride | phenoxymethyl | 2-(1-morpholino)ethyl | H |
| 34/hydrochloride | 2-thienyl | methyl | H |
| 35/hydrochloride | 4-chlorophenoxymethyl | 2-(1-morpholino)ethyl | H |
| 36/hydrochloride | t-butyl | allyl | H |
| 37/hydrochloride | 4-ethoxyphenyl | 2-(1-piperido)ethyl | H |
| 38/hydrochloride | 2-thienyl | 2-(1-piperido)ethyl | H |
| 39/hydrochloride | 4-bromophenyl | allyl | H |
| 40/hydrochloride | 4-chlorophenoxymethyl | 2-(1-piperido)ethyl | H |
| 41/hydrochloride | phenoxymethyl | allyl | H |
| 42/hydrochloride | 3,4-dichlorophenyl | 2-(N,N-diethylamino)ethyl | H |
| 43/hydrochloride | phenyl | n-propyl | H |
| 44/hydrochloride | phenoxymethyl | methyl | H |

TABLE 1-continued

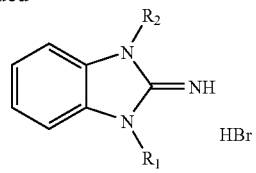

| Compound no./salt | $R_1$ | $R_2$ | R4 |
|---|---|---|---|
| 45/hydrochloride | 4-methoxyphenyl | 2-(1-piperido)ethyl | H |
| 46/hydrochloride | 4-chlorophenoxymethyl | allyl | H |
| 47/hydrochloride | 4-methoxyphenyl | benzyl | H |
| 48/hydrochloride | 4-chlorophenyl | n-propyl | H |
| 49/hydrochloride | 4-ethoxyphenyl | allyl | H |
| 50/hydrochloride | 4-methylphenyl | allyl | H |
| 51/hydrochloride | 3,4-dichlorophenyl | 2-(N,N-dimethylamino)ethyl | H |
| 52/hydrochloride | 4-chlorophenoxymethyl | 4-methylbenzyl | H |
| 53/hydrochloride | 4-chlorophenyl | n-butyl | H |
| 54/hydrochloride | 4-chlorophenyl | methyl | H |
| 55/hydrochloride | phenoxymethyl | 2-(N,N-diethylaminoethyl] | H |
| 56/hydrochloride | 4-chlorophenoxymethyl | 2-(N,N-diethylaminoethyl] | H |
| 57/hydrochloride | 4-chlorophenoxymethyl | methyl | H |
| 58/hydrochloride | 1-naphthyl | methyl | H |
| 59/hydrochloride | t-butyl | 4-chlorobenzyl | H |
| 60/hydrochloride | 4-methylphenyl | n-propyl | H |
| 61/hydrochloride | methyl | n-propyl | H |
| 62/hydrochloride | 4-bromophenyl | n-butyl | H |
| 63/hydrochloride | 4-bromophenyl | benzyl | H |
| 64/hydrochloride | p-chlorophenyl | allyl | H |
| 65/hydrochloride | phenyl | methyl | H |
| 66/hydrochloride | methyl | methyl | H |
| 67/hydrochloride | 2-furyl | benzyl | H |
| 68/hydrochloride | 2-furyl | 4-chlorobenzyl | H |
| 69/hydrochloride | t-butyl | 2-(1-piperido)ethyl | H |
| Novel Compounds | | | |
| 70/hydrobromide | phenoxymethyl | 4-fluorobenzyl | H |
| 71/hydrobromide | —CH$_2$OCH$_2$C$_6$H$_5$ (benzyloxymethyl) | benzyl | H |
| 72/hydrobromide | phenoxymethyl | n-octyl | H |
| 73/hydrobromide | phenoxymethyl | methylene-1-naphthyl | H |
| 74/hydrobromide | phenoxymethyl | n-undecyl | H |
| 75/hydrobromide | phenoxymethyl | benzyl | —CO$_2$C$_2$H$_5$ |
| 76/hydrobromide | phenoxymethyl | 2-(N,N-dibenzylamino)ethyl | H |
| 77/hydrobromide | benzyl | benzyl | H |
| 78/hydrobromide | phenoxymethyl | 4-methoxybenzyl | H |

Process: In general, the compounds of this invention may be prepared by a stepwise alkylation of 2-aminobenzimidazole or a ring-substituted 2-aminobenzimidazole where R$_4$ is other than hydrogen.

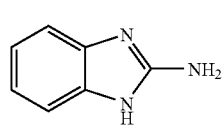 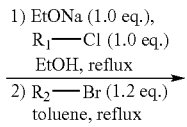

In the first alkylation, the sodium salt of 2-aminobenzimidazole reacts smoothly with alkyl and benzyl chlorides (Joseph, L., *J Med Chem*, 28:601 (1963); Ogura, H., et al., *J Med Chem*, 15:923-926 (1972)). The second alkylation proceeds under conditions of high concentration in refluxing toluene, reacting exclusively at the 3-position of the imidazole moiety (Rehse, K., et al., *Arch Pharm* (*Weinheim*), 328:77-80 (1995)). The precipitation of the product as the hydrobromide salt prohibits additional alkylation and simplifies the purification. Yields after crystallization are low, but sufficient.

Alternatively, as described below with respect to the preparation of a combinatorial library, the compounds can be prepared by a process in which a resin-bound 4-fluoro-3-nitroarene is reacted with an amine having the formula R$_2$—NH$_2$, reduced with tin(II) chloride (Bellamy, F. D., et al., *Tetrahedron Lett*, 25:839-842 (1984)), cyclized with cyanogen bromide (U.S. Pat. No. 4,002,623), and reacted with a mono-substituted epoxide:

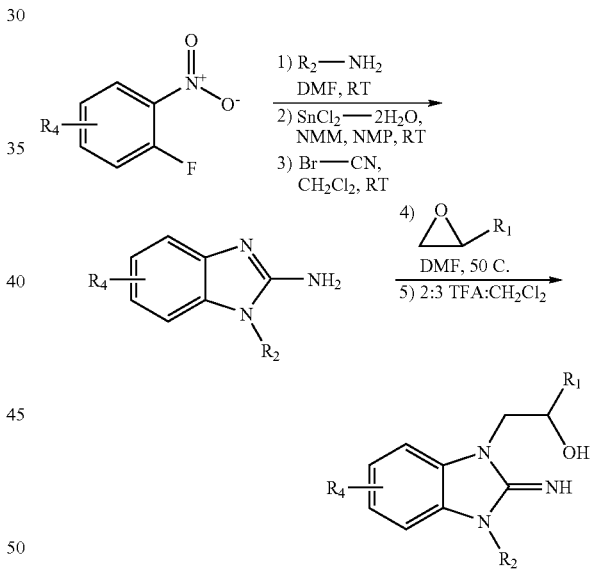

If R$_4$ is a group having the formula CONR$_{16}$R$_{17}$, that group is first introduced by amide coupling with the fluoronitrobenzoic acid.

Compositions: For pharmaceutical use, the compounds are incorporated into compositions or formulations. The compositions will contain pharmaceutically acceptable diluents and/or carriers, i.e. diluents or carriers that are biocompatible and free from undesirable impurities.

For administration by injection and/or infiltration or infusion, the compositions or formulations according to the invention may be suspended or dissolved as known in the art in a vehicle suitable for injection and/or infiltration or infusion. Such vehicles include isotonic saline, buffered or unbuffered and the like. Depending on the intended use, they also may contain other ingredients, including other active ingredients. For example, the compositions may contain augmenting agents for potentiating or prolonging the anesthetic activity, such as those described in U.S. Pat. No. 6,248,345, or ingredients such as isotonicity agents, sodium chloride, pH modifiers, colorants, preservatives, antibodies, enzymes, antibiotics, antifungals, antivirals, other anti-infective agents, and/or diagnostic aids such as radio-opaque dyes, radiolabeled agents, and the like, as known in the art.

However, the compositions of this invention may comprise no more than a simple solution or suspension of a compound or compounds, or a pharmaceutically acceptable salt of a compound, or combination of salts of compounds, in distilled water or in saline.

The compositions may also be in the form of controlled release or sustained release compositions as known in the art, for instance, in matrices of biodegradable or non-biodegradable injectable polymeric microspheres or microcapsules, in liposomes, in emulsions, and the like, for example, as described in U.S. Pat. No. 6,248,345.

For use, the compositions may be prepared in unit dosage forms that are sterilized and then placed within a container such as an ampoule. For instance, for use as a local anesthetic, an amount of such a composition containing an anesthetically or and/or analgesically effective amount of a compound of this invention, i.e. one sufficient to induce anesthesia or analgesia in a patient, is sterilized and placed in such a container.

The compositions of this invention may, as stated above, be prepared in the form of single-dosage units for direct administration to a patient. However, more concentrated compositions may be prepared, from which the more dilute single-unit compositions may then be produced. The more concentrated compositions thus will contain substantially more than an anesthetically or analgesically effective amount of the compound in question.

The novel compounds of this invention may be used per se, or in the form of their pharmaceutically acceptable salts, such as hydrochlorides, hydrobromides, acetates, sulfates, citrates, carbonates, trifluoroacetates and the like. The term "pharmaceutically acceptable salts" is meant to include salts of the compounds in question that are prepared with relatively nontoxic acids or bases, depending on the particular substituents found on the compounds described herein. When compounds of the present invention contain relatively acidic functionalities, salts can be obtained by addition of the desired base, either neat or in a suitable inert solvent. Examples of pharmaceutically acceptable base addition salts include sodium, potassium, calcium, ammonium, organic amino, or magnesium salts, or the like. When compounds of the present invention contain relatively basic functionalities, salts can be obtained by addition of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al., "Pharmaceutical Salts", *Journal of Pharmaceutical Science*, 1977, 66, 1-19).

Compositions will typically contain a single anesthetic or analgesic compound of this invention. However, in some cases it may be advantageous to use a combination of two or more of such compounds; thus the compositions may contain more than one such compound.

Administration: For use as anesthetics, particularly local anesthetics, the compounds (in the form of their compositions) are administered to patients by the usual means known in the art, for example, by injection, infusion, infiltration, irrigation, topically and the like. Injection or infusion can be carried out acutely, or if prolonged local effects are desired, localized anesthetic agents can be administered continuously by means of a gravity drip or infusion pump. When used for perioperative pain control, administration may be done prior to surgery, at the time of surgery, or following surgery, and preceding, during or following administration or effect of a systemic anesthetic. Solid formulations may be shaped to fit a particular location, e.g., articular joints, then surgically placed into a site where release of local anesthetic agent is desired.

If a combination of two or more compounds of this invention is to be administered, they preferably are administered simultaneously, either in the form of a single composition or in separate compositions. They preferably are administered using the same route of administration, but this is not always necessary. For example, two compounds of the invention may be administered together via intramuscular injection or intravenously, or one compound may be administered by intramuscular injection and the other intravenously. Other routes of administration, for example oral or parenteral (intravenous, intramuscular or subcutaneous injection) may be used, as well as direct injection to the central nervous system (intrathecally).

The compounds and compositions of this invention are particularly suitable for use as local spinal and/or epidural anesthetics; however, they may be useful elsewhere as local anesthetics. Thus, formulations of this invention may be administered to intra-articular joints and bursa, and to body spaces or cavities, including pleura, peritoneum, cranium, mediastinum, and pericardium. In a preferred embodiment, potential applications include any condition for which localized anesthesia is desirable.

The uses of the compositions of this invention include both local anesthesia for the relief of pain and motor symptoms as well as local anesthesia for other medical purposes. Other applications include providing localized temporary sympathectomy, e.g., blockade of sympathetic or parasympathetic ganglia to treat a variety of autonomic diseases, including circulatory dysfunction or trigeminal neuralgia. The formulations may also be used to provide a temporary nerve block to treat localized muscle spasm and treatment of retrobulbar conditions, e.g., eye pain.

The uses of the compositions of this invention further include the treatment and/or prophylaxis of neural injury, degeneration, or death. Conditions or disorders suitable for treatment may be acute in onset such as occurs in traumatic brain injury, or chronic or insidious as may occur in neurodegenerative disorders such as ALS. These conditions may be widespread such as occurs in global ischemia following cardiac arrest, drowning, or carbon monoxide poisoning, may be restricted to or preferentially affect specific populations of susceptible neurons, or may involve discrete areas of the nervous system as may occur with stroke resulting from disruption of regional blood flow.

EXAMPLES

The following examples are provided by way of illustration only and not by way of limitation. Those of skill will readily recognize a variety of noncritical parameters that could be changed or modified to yield essentially similar results.

Example 1

Synthesis of 1-benzyl-2-imino-3-(2-hydroxy-3-phenoxypropyl)benzimidazole hydrobromide (1) (Compound #3)

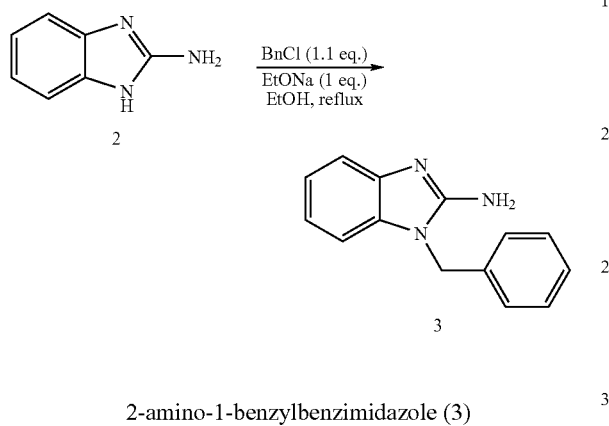

2-amino-1-benzylbenzimidazole (3)

To a solution of 2-aminobenzimidazole (2) (Aldrich, 6 g., 45 mmol) in EtOH (10 mL) was added EtONa (21% in EtOH, 16.83 mL, 45 mmol) and benzyl chloride (5.70 mL, 50 mmol) and the brown solution was refluxed for 3 days under $N_2$ gas. After cooling to room temperature, the reaction mixture was filtered through celite and concentrated in vacuo. The resulting brown solid was filtered hot in 300 mL acetone and crystallized from approximately 100 mL of acetone, and gave 3 as brown crystals (3.91 g., 39%). Recrystallization of the mother liquor afforded additional 3 as brown crystals (0.70 g., 7%). $^1$H-NMR (DMSO-$d_6$) δ 5.27 (s, 2H), 6.61 (s, 2H), 6.82 (t, J=8.8 Hz, 1H), 6.93 (t, J=6.4 Hz, 1H), 7.05 (d, J=8.0 Hz, 1H), 7.15 (d, 7.2 Hz, 1H), 7.20 (d, 6.8 Hz, 2H), 7.24 (d, 7.6 Hz, 1H), 7.31 (t, 7.6 Hz, 2H); $^{13}$C-NMR (DMSO-$d_6$) 45.11, 108.30, 115.19, 118.49, 120.88, 127.39, 127.66, 128.91, 134.60, 137.64, 143.34, 155.46.

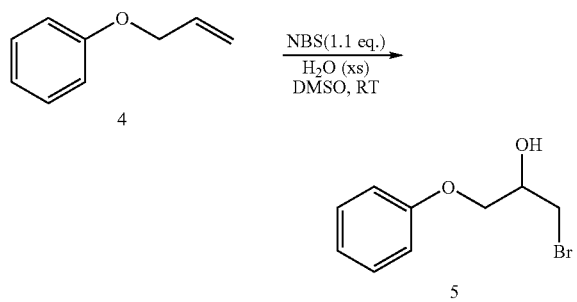

1-bromo-3-phenoxy-propan-2-ol (5)

To a room temperature water cooled solution of allyl phenyl ether (4) (Aldrich, 1.00 g., 7.45 mmol) in 5 mL DMSO: $H_2O$ (4:1) was added NBS (1.45 g., 8.15 mmol) as a solid. After 5-10 minutes, the reaction was added to a separation funnel with 100 mL $Et_2O$ and washed three times with 100 mL water, then 100 mL brine solution. The ether layer was dried over $MgSO_4$ and concentrated in vacuo to yield a pale yellow oil (1.59 g., 92%), which was used as is without further purification.

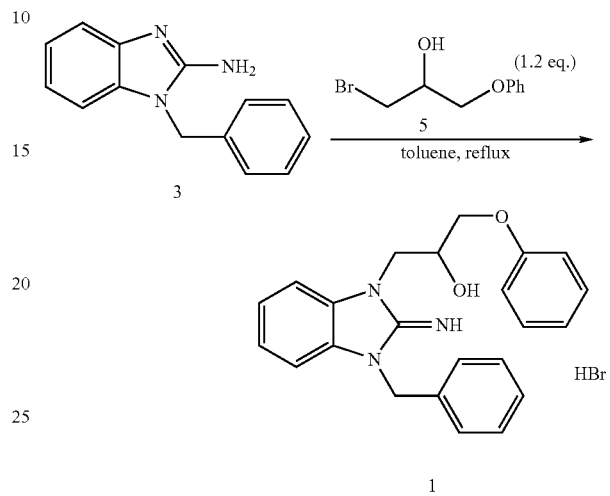

1-benzyl-2-imino-3-(2-hydroxy-3-phenoxypropyl) benzimidazole hydrobromide (1)

To a solution of 1-bromo-3-phenoxy-propan-2-ol (5) (248 mg., 1.07 mmol.) in toluene (2 mL.) was added 2-amino-1-benzylbenzimidazole (3) (200 mg., 0.90 mmol) and the mixture was heated at reflux overnight under $N_2$ gas. The reaction mixture was cooled to room temperature and filtered. Crystallization of the collected solid from isopropanol gave 1 as white crystals (85 mg., 23%). Recrystallization of the mother liquor afforded additional 1 as white crystals (70 mg., 19%). $^1$H-NMR (DMSO-$d_6$) δ 4.12 (s, 2H), 4.33 (s, 1H), 4.43 (s, 2H), 5.57 (s, 2H), 6.96 (m, 3H), 7.21-7.38 (m, 10H), 7.46 (d, J=8.0 Hz, 1H), 7.62 (d, J=7.6 Hz, 1H), 9.18 (s, 2H); $^{13}$C-NMR (DMSO-$d_6$) δ 45.58, 46.10, 66.54, 69.43, 110.53, 111.11, 120.71, 123.39, 123.47, 127.11, 127.91, 128.72, 129.39, 129.45, 130.39, 134.56, 150.27, 157.67, 158.33.

Example 2

Preparation of Library of Compounds Using a Combinatorial Method

A library of compounds in which $R_4$ was various groups having the formula $CONHR_{17}$ was prepared by the process described above using 4-fluoro-3-nitrobenzoic acid, as follows:

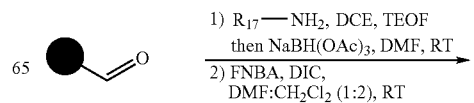

1) $R_{17}$—$NH_2$, DCE, TEOF
then NaBH(OAc)$_3$, DMF, RT
2) FNBA, DIC,
DMF:$CH_2Cl_2$ (1:2), RT

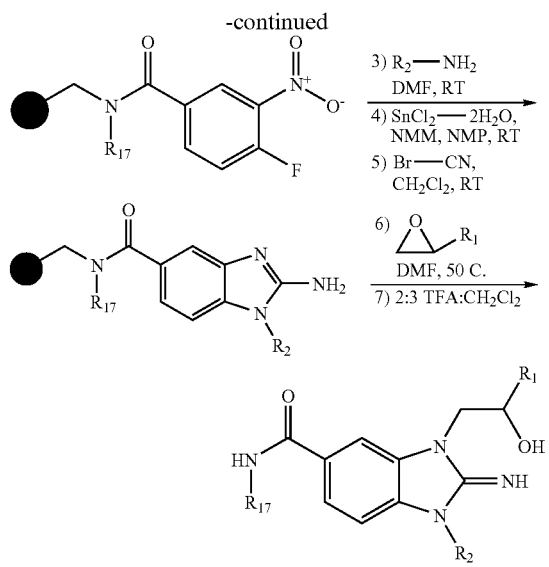

Aldehyde resin was mixed with a primary amine ($R_{17}$—$NH_2$) in dichloroethane (DCE), triethylorthoformate (TEOF), and DMF (containing 1% acetic acid) in a 1:1:1 ratio. After shaken overnight, sodium triacetoxyborohydride (20 eq.) dissolved in DMF was added (Abdel-Magid, A. F., et al., *Tetrahedron Lett,* 31:5595-5598 (1990)). After the mixture was shaken at room temperature overnight, the resin was filtered and washed with DMF (3×5 mL), MeOH (3×5 mL), DMF (3×5 mL), MeOH (3×5 mL), and $CH_2Cl_2$ (3×5 mL). The resin was washed twice with 5 mL DMF containing 1% Hunig's base. To the filtered resin was added a mixture of 4-fluoro-3-nitrobenzoic acid (FNBA, 10 eq.) and diisopropylcarbodiimide (DIC, 5 eq.) in 2:1 DMF:DCM. After shaking at room temperature overnight, the resin was filtered and washed with DMF (3×5 mL) and $CH_2Cl_2$ (3×5 mL).

The resin was shaken with a primary amine ($R_2$—$NH_2$) in DMF for 8 hrs, filtered, and washed with DMF (6×5 mL), MeOH (3×5 mL), and $CH_2Cl_2$ (3×5 mL). The aryl nitro group was reduced by the addition of tin(II) chloride dihydrate (20 eq., >2 M) and N-methyl morpholine (NMM, 20 eq.) in N-methylpyrrolidinone (NMP). After shaken at room temperature overnight, the resin was filtered and washed with NMP (3×5 mL), MeOH (3×5 mL), and $CH_2Cl_2$ (3×5 mL). The resulting resin was shaken at room temperature with cyanogen bromide (5 eq.) overnight, filtered, and washed with $CH_2Cl_2$ (3×5 mL), MeOH (3×5 mL), and $CH_2Cl_2$ (3×5 mL). To produce a free amine, the resin was shaken for 30 min. in $CH_2Cl_2$ with the addition of sodium methoxide in methanol, filtered, and washed with $CH_2Cl_2$ (4×5 mL).

In the final diversification step, the resin was heated at 50° C. in DMF with a mono-substituted epoxide [$R_1CH(-CH_2O-)$]. After shaking for 2 to 4 days the resin was filtered and washed with DMF (5×5 mL), MeOH (3×5 mL), and $CH_2Cl_2$ (3×5 mL). The resin-bound benzimidazole was cleaved from the solid-support by treatment with TFA:$CH_2Cl_2$ (2:3) for 1 hour at room temperature. The library contained a total of 10,560 compounds, prepared using 32 species of group $R_{17}$, 33 of group $R_2$ and 10 of group $R_1$. The library of compounds is depicted in Table 2:

TABLE 2

| # | Structure | R Group | Common Name |
|---|---|---|---|
| 1 | —$CH_3$ | 17 | methyl |
| 2 | —$CH_2CH_3$ | 17 | ethyl |
| 3 | —$CH_2CH_2CH_3$ | 17 | propyl |
| 4 | pyrazole-X | 17 | 3-pyrazolyl |
| 5 | cyclopentyl-X | 17 | cyclopentyl |
| 6 | -Ph | 17 | phenyl |
| 7 | pyrimidine-X | 17 | 2-pyrimidinyl |
| 8 | furan-CH2-X | 17 | furfuryl |
| 9 | tetrahydrofuran-CH2-X | 17 | tetrahydrofurfuryl |
| 10 | isoxazolone-X | 17 | 3-keto-4,5-dihydro-isoxazolyl |
| 11 | —$CH_2CH_2OCH_2CH_2CH_3$ | 17 | propoxyethyl |
| 12 | -Bn | 17 | benzyl |
| 13 | pyridine-CH2-X | 17 | picolyl |
| 14 | thiophene-CH2-X | 17 | 2-thienyl |
| 15 | —$CH_2CH_2N(CH_2)_4$ | 17 | N-ethyl-pyrrolidine |
| 16 | —$CH_2CH_2COOCH_2CH_3$ | 17 | propoxylate ethyl ester |
| 17 | -Bn-4-Me | 17 | 4-methylbenzyl |

TABLE 2-continued

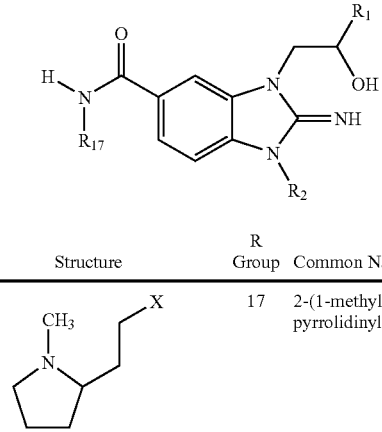
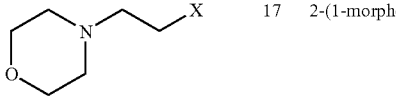

| # | Structure | R Group | Common Name |
|---|---|---|---|
| 18 | 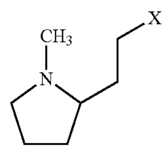 | 17 | 2-(1-methyl-pyrrolidinyl)ethyl |
| 19 | 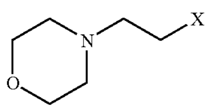 | 17 | 2-(1-morpholino)ethyl |
| 20 | -Bn-3-OMe | 17 | 3-methoxybenzyl |
| 21 | -Bn-3-Cl | 17 | 3-chlorobenzyl |
| 22 | 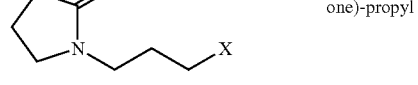 | 17 | 3-(1-pyrrolidinyl-2-one)-propyl |
| 23 | -Bn-4-NMe$_2$ | 17 | 4-(dimethylamino)-benzyl |
| 24 | 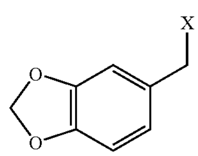 | 17 | piperonyl |
| 25 | -Bn-4-NO$_2$ | 17 | 4-nitrobenzyl |
| 26 | 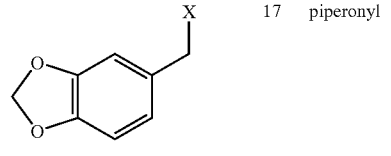 | 17 | 3-(4-methyl-1-piperazinyl)-propyl |
| 27 | 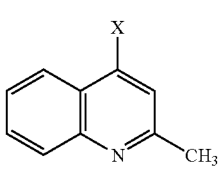 | 17 | 2-methyl-4-quinolinyl |
| 28 | -Bn-3-CF$_3$ | 17 | 3-trifluoromethyl-benzyl |
| 29 | -Bn-2,6-Cl | 17 | 2,6-dichlorobenzyl |
| 30 | -Bn-4-SO$_2$Me | 17 | 4-(methylsulfonyl)-benzyl |
| 31 | -Bn-3,4,5-OMe | 17 | 3,4,5-trimethoxy-benzyl |
| 32 | -CH$_2$CH$_2$CHPh$_2$ | 17 | 3,3-diphenylpropyl |
| 1 | —CH(CH$_3$)$_2$ | 2 | isopropyl |
| 2 | —CH$_2$CH$_2$OH | 2 | 2-hydroxyethyl |
| 3 | 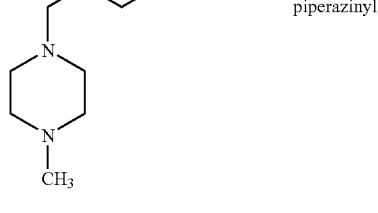 | 2 | 3-pyrazolyl |
| 4 | —CH$_2$CH$_2$CH(CH$_3$)$_2$ | 2 | isopentyl |
| 5 | -Ph | 2 | phenyl |
| 6 | 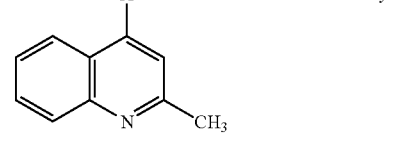 | 2 | 3-pyridyl |
| 7 |  | 2 | 2-pyrimidinyl |
| 8 |  | 2 | furfuryl |
| 9 |  | 2 | cyclohexyl |
| 10 |  | 2 | N-piperidinyl |
| 11 |  | 2 | tetrahydrofurfuryl |
| 12 | —CH$_2$CH$_2$OCH$_2$CH$_2$CH$_3$ | 2 | propoxyethyl |
| 13 | -Bn | 2 | benzyl |
| 14 |  | 2 | 2-picolyl |

TABLE 2-continued

| # | Structure | R Group | Common Name |
|---|---|---|---|
| 15 | (2-thienylmethyl structure) | 2 | 2-thienylmethyl |
| 16 | —CH₂CH₂N(CH₂)₄ | 2 | 2-(1-pyrrolidinyl)ethyl |
| 17 | —CH₂CH₂COOCH₂CH₃ | 2 | propoxylate ethyl ester |
| 18 | -Bn-4-Me | 2 | 4-methylbenzyl |
| 19 | (quinuclidinyl structure) | 2 | 3-quinuclidinyl |
| 20 | (piperidino-ethyl structure) | 2 | 2-(1-piperidino)-ethyl |
| 21 | (morpholino-ethyl structure) | 2 | 2-(1-morpholino)-ethyl |
| 22 | (indanyl structure) | 2 | 1-indanyl |
| 23 | -Bn-3-OMe | 2 | 3-methoxybenzyl |
| 24 | -Bn-3-Cl | 2 | 3-chlorobenzyl |
| 25 | (morpholino-propyl structure) | 2 | 3-(1-morpholino)-propyl |
| 26 | -Bn-4-NMe₂ | 2 | 4-(dimethylamino)-benzyl |
| 27 | (piperonyl structure) | 2 | piperonyl |
| 28 | -Bn-4-NO₂ | 2 | 4-nitrobenzyl |
| 29 | (4-methylpiperazinyl-propyl structure) | 2 | 3-(4-methyl-1-piperazinyl)-propyl |
| 30 | -Bn-3-CF₃ | 2 | 3-trifluoromethyl-benzyl |
| 31 | -Bn-2,4-Cl | 2 | 2,4-dichlorobenzyl |
| 32 | -Bn-4-SO₂Me | 2 | 4-(methylsulfonyl)-benzyl |
| 33 | -Bn-3,4,5-OMe | 2 | 3,4,5-trimethoxy-benzyl |
| 1 | —CH2OPh | 1 | phenoxymethyl |
| 2 | —CH2OCH(CH3)2 | 1 | isopropoxymethyl |
| 3 | —CH2OPh-4-OMe | 1 | (4-methoxy)-phenoxymethyl |
| 4 | —CH2OPh-4-C(CH3)3 | 1 | (4-t-butyl)-phenoxymethyl |
| 5 | (furfuryloxymethyl structure) | 1 | 2-furfuryloxymethyl |
| 6 | —CH2OPh-2-Me | 1 | 2-methylphenoxymethyl |
| 7 | —CH2OPh-4-Cl | 1 | 4-chlorophenoxymethyl |
| 8 | -Ph | 1 | phenyl |
| 9 | (pyridylmethyl structure) | 1 | 2-carbamyl-5-indolyl-oxymethyl |
| 10 | —CH2OPh-4-NO2 | 1 | 4-nitrophenoxymethyl |

Example 3

Testing for In Vitro Activity

In vitro testing of the compounds of Table 1 was conducted as follows, using the assay protocol as described by Catterall, et al. (Catterall, W. A., et al., *J Biol Chem*, 254:11379-11387 (1979))

The following solutions were prepared:
1) Standard Binding Medium:

| Component | Amount (1 L preparation) |
|---|---|
| albumin (BSA), 1 mg/mL | 1000 mg. |
| choline chloride, 130 mM | 18.15 g. |
| HEPES (N-2-hydroxyethyl-piperazine-N-2-ethanesulfonic acid), 50 mM | 11.91 g. |
| glucose, 5.5 mM | 990 mg. |
| potassium chloride, 5.4 mM | 400 mg. |
| magnesium sulfate, 0.8 mM | 96 mg. |

The Standard Binding Medium was made in deionized water, adjusted to pH 7.4 with Tris base, and stored at 4° C. for up to 1 week.

2) Wash Buffer:

| Component | Amount (4 L prep.) |
|---|---|
| choline chloride, 163 mM | 79.659 g |
| HEPES, 5 mM | 4.170 g |
| albumin (BSA), 1 mg/mL | 3.500 g. |
| calcium chloride, 1.8 mM | 0.926 g. |
| magnesium sulfate, 0.8 mM | 0.337 g. |

The Wash Buffer was made in deionized water, adjusted to pH 7.4 with Tris base, and stored at 4° C. for up to 1 week.

Membrane Preparation

The following solutions were prepared:
1) Membrane Solution A:

| Component | Amount (500 mL prep.) |
|---|---|
| sucrose, 0.32 M | 54.77 g. |
| sodium phosphate, monobasic, 5 mM | 345 mg. |
| p-toluenesulfonyl fluoride, 0.1 mM | 9 mg. |

The Membrane Solution A was made in deionized water, adjusted to pH 7.4 with sodium hydroxide, and stored at 4° C. for up to 2 months.

2) Membrane Solution B:

| Component | Amount (250 mL prep.) |
|---|---|
| choline chloride, 260 mM | 9.07 g. |
| HEPES, 100 mM | 5.96 g. |
| glucose, 11 mM | 495 mg. |
| potassium chloride, 10.8 mM | 202 mg. |
| magnesium chloride, 1.6 mM | 48 mg. |

The Membrane Solution B was made in deionized water, adjusted to pH 7.4 with Tris base, and stored at 4° C. for up to 2 months.

Male Sprague-Dawley rat forebrain(s) were extracted, washed with Membrane Solution A, and homogenized in 9 mL/g of Membrane Solution A. The homogenate was centrifuged for 60 minutes at 17,000 g., and the supernatant liquid was removed. The membranes were resuspended in 3.3 mL/g of Membrane Solution A, then incubated at 4° C. for 30 minutes. 3.3 mL/g of Membrane Solution B was added, and the membranes were frozen in 1 mL aliquots at −80° C. for up to 4 days. The thus prepared Membrane Preparations were thawed on ice immediately before the Assay.

Assay

An assay was prepared in 96-well microtiter plates, having the following composition, and having 100 μL final volume:
60 μL Standard Binding Medium
20 μL [$^3$H]Saxitoxin: 10 nM (Amersham Pharmacia: TRK-877)
10 μL of the test Compound: 100 μM (contains less than 2% DMSO)
10 μL Membrane Preparation The mixture was incubated for 25 minutes at room temperature (25° C.), then filtered over a Packard RG glass fiber filters, and washed 5× with 200 μL of Wash Buffer per well using a 96-well plate Cell Harvester (Packard). Immediately, the filter was dried and counted for 3 minutes. Non-specific binding is determined using 10 μL of 10 μM TTX (in place of the test Compound) and is 5-10% of the total binding.

Activity of the test compounds is expressed in terms of percent inhibition and, for some compounds, the concentration at which 50% inhibition is achieved ($IC_{50}$) (based on an 11-point dose-response curve. Results of this assay for the compounds in Table 1 are given in the following Table 3. A dash (-) indicates less than 10% inhibition was observed in this test.

TABLE 3

| In vitro testing | | |
|---|---|---|
| Compound no. | % inhibition | $IC_{50}$ (μM) |
| 1 | 59 | 15 |
| 2 | 46 | 21 |
| 3 | 52 | 21 |
| 4 | 47 | 21 |
| 5 | 38 | 41 |
| 6 | 52 | 43 |
| 7 | 51 | 60 |
| 8 | 41 | 87 |
| 9 | 46 | 89 |
| 10 | 42 | 96 |
| 11 | 48 | 155 |
| 12 | 59 | 34 |
| 13 | 46 | 232 |
| 14 | 16 | |
| 15 | 11 | |
| 16 | 17 | |
| 17 | 11 | |
| 18 | 11 | |
| 19 | 11 | |
| 20 | 12 | |
| 21 | 13 | |
| 22 | 14 | 210 |
| 23 | 15 | |
| 24 | 16 | |
| 25 | 16 | |
| 26 | 17 | |
| 27 | 17 | |
| 28 | 17 | |
| 29 | 18 | |
| 30 | 18 | |
| 31 | 19 | |
| 32 | 20 | |
| 33 | 20 | |
| 34 | 20 | |
| 35 | 20 | |
| 36 | 22 | |
| 37 | 22 | |
| 38 | 22 | |

TABLE 3-continued

| In vitro testing | | |
|---|---|---|
| Compound no. | % inhibition | $IC_{50}$ (μM) |
| 39 | 24 | |
| 40 | 24 | |
| 41 | 25 | |
| 42 | 25 | |
| 43 | 26 | |
| 44 | 27 | |
| 45 | 28 | |
| 46 | 29 | |
| 47 | 32 | |
| 48 | 32 | |
| 49 | 32 | |
| 50 | 33 | |
| 51 | 36 | |
| 52 | 37 | |
| 53 | — | |
| 54 | — | |
| 55 | — | |
| 56 | — | |
| 57 | — | |
| 58 | — | |
| 59 | — | |
| 60 | — | |
| 61 | — | |
| 62 | — | |
| 63 | — | |
| 64 | — | |
| 65 | — | |
| 66 | — | |
| 67 | — | |
| 68 | — | |
| 69 | 18 | |
| 70 | 26 | 97 |
| 71 | 34 | 30 |
| 72 | 20 | 66 |
| 73 | — | 107 |
| 74 | 33 | 117 |
| 75 | — | 118 |
| 76 | — | 100 |
| 77 | 27 | 81 |
| 78 | 17 | 67 |

Example 5

Testing for In Vivo Activity

Compounds of Table 1 were tested for activity in vivo by the following method, using modifications of the assay protocols described by Drasner et al. (Drasner, K., et al., *Anesthesiology*, 80:847-852 (1994); Sakura, S., et al., *Anesthesiology*, 85:1184-1189 (1996))

Male Sprague-Dawley rats (200-300 g) were implanted with intrathecal catheters according to the procedure described by Drasner et al. Rats were placed in a horizontal restraint and sensory function was assessed using the tail-flick test. The tail was placed over a slit through which a bean of light was projected with latency to movement as the measured end-point. The heat was shut off if there was no response by 8 seconds (cut-off).

Test compounds were dissolved at the desired concentration in aqueous 2.5% glucose solution ("Glu") (or aqueous polyethylene glycol ("PEG") (average MW=1000) solution in cases of low solubility). Rats were given an intrathecal injection of the test compound of 60 μL at a rate of approximately 1 μL/sec. Tail sensory function was assessed 5 minutes, 1 hour, 1 day, and 4 days post-injection.

The results of this assay are shown in the following Table 4. Tail sensory function is expressed in terms of % Maximal Possible Effect (MPE), which is defined as calculated as {(tail-flick latency−baseline)/(cut-off−baseline)}×100. Thus, a compound producing complete anesthesia or unresponsiveness to the heat stimulus would receive a score of 100.

TABLE 4

| In vivo testing | | | | | |
|---|---|---|---|---|---|
| Compound | Conc. (M) | Formulation | Animals Tested (N) | Average % MPE 5 minutes | Average % MPE Day 4 |
| 1 | 3.30 | 10% PEG | 2 | 100 | 3 |
| 2 | 4.53 | 10% PEG | 2 | 100 | 1 |
| 3 | 4.00 | 10% PEG | 3 | 100 | −2 |
| 3 | 4.23 | 2.5% Glu | 3 | 76 | 6 |
| 4 | 4.30 | 10% PEG | 2 | 100 | −2 |
| 5 | 7.95 | 10% PEG | 2 | 100 | 7 |
| 6 | 4.65 | saline | 2 | 93 | −5 |
| 6 | 4.65 | 10% PEG | 2 | 80 | −6 |
| 6 | 11.62 | 10% PEG | 2 | 100 | 1 |
| 6 | 11.62 | 2.5% Glu | 4 | 100 | 21 |
| 7 | 8.00 | 10% PEG | 2 | 100 | 32 |
| 8 | 7.00 | 10% PEG | 2 | 100 | 1 |
| 8 | 14.40 | 10% PEG | 2 | 100 | 18 |
| 8 | 14.40 | 2.5% Glu | 3 | 100 | 47 |
| 9 | 4.05 | 10% PEG | 2 | 100 | 34 |
| 10 | 4.00 | 2.5% Glu | 3 | 26 | 19 |
| 11 | 3.51 | 10% PEG | 2 | 34 | 18 |
| 22 | 12.00 | 10% PEG | 2 | 100 | 11 |
| 22 | 12.00 | 2.5% Glu | 2 | 100 | 8 |
| 22 | 24.20 | 2.5% Glu | 2 | 100 | −2 |
| 70 | 4.83 | 10% PEG | 3 | 83 | 4 |
| 71 | 5.90 | 10% PEG | 2 | 100 | 2 |
| 78 | 2.93 | 2.5% Glu | 2 | 11 | −4 |
| — | — | 10% PEG | 2 | 5 | −3 |
| — | — | 2.5% Glu | 2 | 2 | 1 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for blocking voltage-sensitive sodium channels of neuronal in a mammalian subject in need of blockage of voltage-sensitive channels of neuronal mammalian cells comprising administering to said subject an effective amount of a compound of the formula

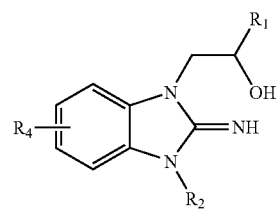

in which $R_1$ is 4-chlorophenoxymethyl;

$R_2$ is benzyl and $R_4$ is H or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 7,868,028 B2 |
| APPLICATION NO. | : 10/174055 |
| DATED | : January 11, 2011 |
| INVENTOR(S) | : Kenneth Drasner and Kevin T. Weber |

It is certified that error appears in the above-identified patent and that said Letters Patent is hereby corrected as shown below:

In column 28, line 46, should read "nels of neuronal mammalian cells in a mammalian subject in need of blockage"

Signed and Sealed this
Fifth Day of April, 2011

David J. Kappos
*Director of the United States Patent and Trademark Office*